(12) United States Patent
Breyne et al.

(10) Patent No.: US 6,719,925 B1
(45) Date of Patent: Apr. 13, 2004

(54) NAPHTHOPYRANS WITH A HETEROCYCLE IN THE 5, 6-POSITION, PREPARATION, AND (CO)POLYMER COMPOSITIONS AND MATRICES CONTAINING THEM

(75) Inventors: Olivier Breyne, Lyons (FR); You-Ping Chan, Lyons (FR); Patrick Jean, Lyons (FR)

(73) Assignee: Corning SAS, Avon (FR)

( * ) Notice: Subject to any disclaimer, the term of this patent is extended or adjusted under 35 U.S.C. 154(b) by 0 days.

(21) Appl. No.: 09/706,122

(22) Filed: Nov. 3, 2000

(30) Foreign Application Priority Data

Nov. 4, 1999 (FR) .......................... 99 13791

(51) Int. Cl.[7] .............................. G02B 5/28; G02C 7/10; C07D 311/92; C07D 491/22; C07D 498/22
(52) U.S. Cl. .................. 252/586; 351/163; 524/94; 524/109; 524/110; 524/111; 548/421; 549/248; 549/383
(58) Field of Search ................ 252/586; 548/421; 524/94, 109, 110, 111; 549/298, 383; 351/162, 163

(56) References Cited

U.S. PATENT DOCUMENTS

| | | | |
|---|---|---|---|
| 3,567,605 A | 3/1971 | Becker ........................ 204/158 |
| 3,627,690 A | 12/1971 | Casella et al. | |
| 4,826,977 A | 5/1989 | Heller et al. .................. 544/70 |
| 5,200,116 A | 4/1993 | Heller ......................... 252/586 |
| 5,238,981 A | 8/1993 | Knowles ...................... 524/110 |
| 5,411,679 A | 5/1995 | Kumar ......................... 252/586 |
| 5,429,774 A | 7/1995 | Kumar ......................... 252/586 |
| 5,451,344 A | 9/1995 | Knowles ....................... 252/586 |
| 5,458,814 A | 10/1995 | Kumar et al. ................. 252/586 |
| 5,645,767 A | 7/1997 | Van Gemert ................... 252/586 |
| 5,651,923 A | 7/1997 | Kumar ......................... 252/586 |
| 5,674,432 A | * 10/1997 | Knowles et al. ............... 252/586 |
| 5,698,141 A | 12/1997 | Kumar ......................... 252/586 |
| 5,783,116 A | 7/1998 | Lin ............................ 252/586 |
| 5,811,034 A | * 9/1998 | Lin ............................ 252/586 |
| 6,022,497 A | * 2/2000 | Kumar ......................... 252/586 |
| 6,203,729 B1 | * 3/2001 | Breyne ........................ 252/586 |
| 6,379,591 B1 | * 4/2002 | Breyne ........................ 252/586 |

FOREIGN PATENT DOCUMENTS

| | | |
|---|---|---|
| EP | 562 915 | 7/2000 |
| FR | 2718447 | 10/1995 |
| FR | 2762845 | 11/1998 |
| WO | WO 94/22850 | 10/1994 |
| WO | WO 95/05382 | 2/1995 |
| WO | WO96/14596 | 5/1996 |
| WO | WO 97/21698 | 6/1997 |

OTHER PUBLICATIONS

Lebouc et al. "New Synthesis Routes to 5,6–Dicarboxy Chromans", J. Chem. Research(5), 1980, 187.*

Wendeborn et al. "Polymer Bound 3,5–Cyclohexylene–1, 2–diols as Core Structures for the Development of Small Molecule Libraries", Synlett (1998), (8), 865–868.*

Zhang et al., Free Energy and Entropy Changes in vertical and Nonvertical Triplet Energy Transfer Processes between Rigid and Nonrigid Molecules. A Laser Photolysis Study, J. Am. Chem. Soc. 1993, 115, pp. 3670–3673.

Sato et al., New and Convenient Synthesis of 2–Substituted 2,3–Dihydro–1H–benz[de]isoquinolin–1–ones, Bull. Chem. Soc. Jpn., 61, 2238–2240 (1988).

Bailey et al., Reduction of Cyclic Anhydrides with NaBH4, Versatile Lactone Synthesis, J. Org. Chem., vol. 35, No. 10, 1970, pp. 3574–3576.

(List continued on next page.)

*Primary Examiner*—Richard D. Lovering
(74) *Attorney, Agent, or Firm*—Siwen Chen

(57) ABSTRACT

The present invention relates to novel compounds of the naphthopyran type with a fused heterocycle in the 5,6-position. These compounds have formula (I) or (II) given below:

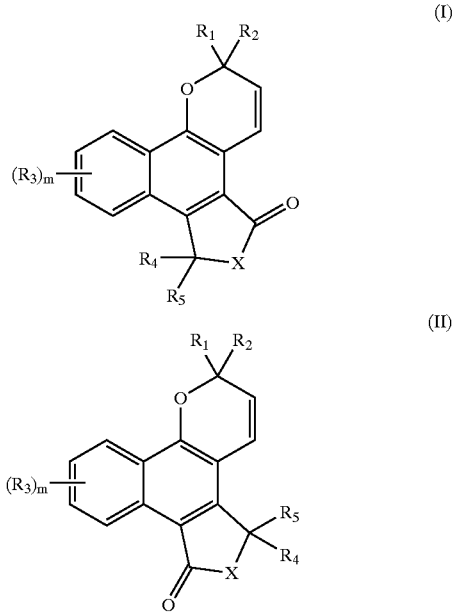

These compounds (I) or (II) have valuable photochromic properties. The invention further relates to their preparation, to their applications as photochromic substances, and to the (co)polymer compositions and matrices containing them.

37 Claims, No Drawings

OTHER PUBLICATIONS

Kotsuki et al., The Reactions of ∝–Alkoxy–Substituted Styrenes with Dimethyl Acetylenedicarboxylate and Dimethyl Fumarate Novel Adducts in the Reaction with Dimethyl Fumarate, Bull. Chem. Soc. Jpn., 67, pp. 599–602, 1994.

J.C. Crano et al., Spiroxazines and their use in photochromic lenses, Applied Photochromic Polymers Systems, Chapter 2, 1992.

Canonne et al., Tetrahedron vol. 44, No. 10, pp. 2903–2912, 1988.

* cited by examiner

NAPHTHOPYRANS WITH A HETEROCYCLE IN THE 5, 6-POSITION, PREPARATION, AND (CO)POLYMER COMPOSITIONS AND MATRICES CONTAINING THEM

This application claims the benefit of priority of FR Application No. 99 13791, filed Nov. 4, 1999, entitled Naphthopyrans With A Heterocycle In The 5,6-Position, Preparation, And (Co)Polymer Compositons And Matrices Containing Them, of Breyne et al.

The present invention relates to novel compounds of the fused naphthopyran type which have photochromic properties in particular. It further relates to the photochromic compositions and photochromic ophthalmic articles (for example lenses) containing said naphthopyrans. The invention further encompasses the preparation of these novel compounds.

Photochromic compounds are capable of changing color under the influence of a poly- or monochromatic light (for example UV) and of returning to their initial color when the light irradiation ceases or under the influence of temperature and/or a different poly- or monochromatic light from the first.

Photochromic compounds are applicable in various fields, for example for the manufacture of ophthalmic lenses, contact lenses, sunglasses, filters, optics for movie cameras, ordinary cameras or other optical and observational devices, glass panes, decorative objects or display elements, or for the storage of data by optical recording (coding).

In the field of ophthalmic optics and particularly spectacles, a photochromic lens, comprising one or more photochromic compounds, must have:
- a high transmission in the absence of ultraviolet,
- a low transmission (high colorability) under solar irradiation,
- appropriate coloration and decolorization kinetics,
- a tint acceptable to the consumer (preferably gray or brown), preferably with maintenance of the chosen tint during the coloration and decolorization of the lens,
- maintenance of the performance characteristics and the properties over the temperature range 0–40° C., and
- a substantial durability because the intended objectives are sophisticated and hence expensive corrective lenses.

These lens characteristics are in fact determined by the active photochromic compounds which the lens contains, it also being necessary for said compounds to be perfectly compatible with the organic, mineral or even hybrid substrate of which the lens is made.

It should furthermore be noted that, to obtain a gray or brown tint, it may be necessary to use at least two photochromic substances of different colors, i.e. having different maximum absorption wavelengths in the visible. This association makes yet more demands on the photochromic compounds. In particular, the coloration and decolorization kinetics of the (two or more) associated active photochromic compounds must be substantially identical. The same applies to their stability over time and also to their compatibility with a plastic or mineral substrate.

The benzopyrans or naphthopyrans described in the following patents or patent applications may be mentioned among the numerous photochromic compounds described in the prior at: U.S. Pat. No. 3,567,605, U.S. Pat. No. 3,627,690, U.S. Pat. No. 4,826,977, U.S. Pat. No. 5,200,116, U.S. Pat. No. 5,238,981, U.S. Pat. No. 5,411,679, U.S. Pat. No. 5,429,744, U.S. Pat. No. 5,451,344, U.S. Pat. No. 5,458,814, U.S. Pat. No. 5,651,923, U.S. Pat. No. 5,645,767, U.S. Pat. No. 5,698,141, U.S. Pat. No. 5,783,116, WO-A-95 05382, FR-A-2 718 447, WO-A-96 14596 and WO-A-97 21698, said compounds having the reduced formulae below:

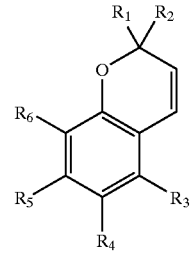
Benzopyrans

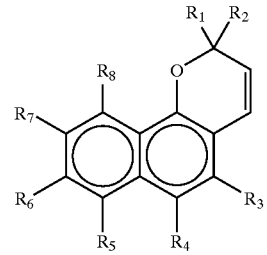
Naphthopyrans

U.S. Pat. No. 5,783,116 more specifically describes naphthopyrans of the following general structure:

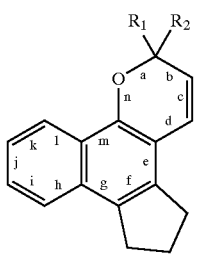 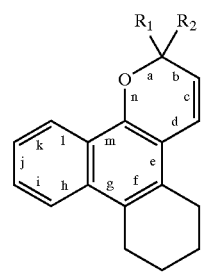

U.S. Pat. No. 5,811,034 claims the following general structure in particular:

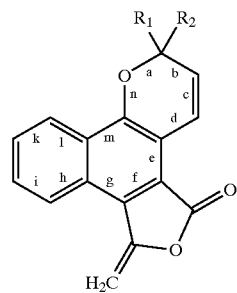

US-A-5 811 034

These compounds are said to satisfy the specifications defined above. In reality, although these compounds do indeed have one or more of the desired basic properties, such as a high transmission in the absence of ultraviolet and a high colorability under solar irradiation, none of the compounds described hitherto have the complete combination of desired properties which is necessary for the production of satisfactory articles. In particular, none of these compounds is intrinsically gray or brown and there is still a need to use a complementary photochromic substance in order to obtain one of these two tints.

In this context, it is to the inventors' credit that they took an interest in this type of derivative as a basis for the development of novel photochromic substances, and that they are proposing a novel family of molecules possessing particularly advantageous photochromic properties.

Thus, according to a first feature, the present invention relates to compounds of formula (I) or (II):

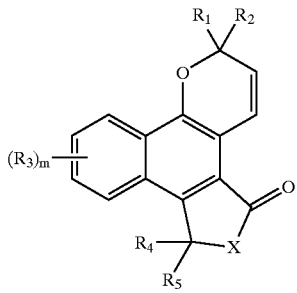

(I)

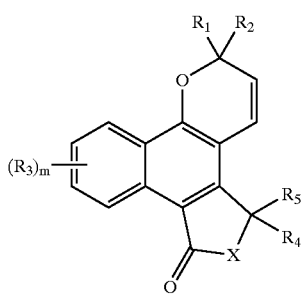

(II)

in which:
  X is an oxygen or NR$_6$, R$_6$ being a hydrogen, a linear or branched alkyl group containing from 1 to 12 carbon atoms, a cycloalkyl group containing from 3 to 12 carbon atoms or an aryl or heteroaryl group containing in its basic structure 6 to 24 carbon atoms or, respectively, 4 to 24 carbon atoms and at least one heteroatom selected from sulfur, oxygen and nitrogen, said basic structure optionally being substituted by at least one substituent selected from a linear or branched alkyl containing 1 to 12 carbon atoms, a linear or branched alkoxy containing 1 to 12 carbon atoms, a halogen and a hydroxy;
  R$_4$ and R$_5$, which are identical or different, independently are a hydrogen, a hydroxy or a linear or branched alkyl group containing 1 to 6 carbon atoms, or together form an oxo group (=O);
  R$_1$ and R$_2$, which are identical or different, independently are:
    hydrogen,
    a linear or branched alkyl group containing from 1 to 12 carbon atoms,
    a cycloalkyl group containing from 3 to 12 carbon atoms,
    an aryl or heteroaryl group containing in its basic structure 6 to 24 carbon atoms or, respectively, 4 to 24 carbon atoms and at least one heteroatom selected from sulfur, oxygen and nitrogen, said basic structure optionally being substituted by at least one substituent selected from the group of substituents given below:
      a halogen, especially fluorine, chlorine or bromine,
      a hydroxy,
      a linear or branched alkyl group containing from 1 to 12 carbon atoms,
      a linear or branched alkoxy group containing from 1 to 12 carbon atoms,
      a haloalkyl or haloalkoxy group corresponding respectively to the above (C$_1$–C$_{12}$)alkyl or (C$_1$–C$_{12}$)alkoxy groups substituted by at least one halogen atom, especially a fluoroalkyl group of this type,
      a phenoxy or naphthoxy group optionally substituted by at least one linear or branched alkyl or alkoxy group containing from 1 to 12 carbon atoms,
      a linear or branched alkenyl group containing from 2 to 12 carbon atoms, especially the vinyl group or the allyl group,
      a group —NH$_2$,
      a group —NHR, R being a linear or branched alkyl group containing from 1 to 6 carbon atoms or a phenyl optionally substituted by at least one linear or branched alkyl containing from 1 to 6 carbon atoms,
      a group:

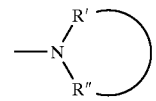

R' and R", which are identical or different, independently being a linear or branched alkyl group containing from 1 to 6 carbon atoms or a phenyl optionally substituted by at least one linear or branched alkyl containing 1 to 6 carbon atoms, or, together with the nitrogen atom to which they are bonded, being a 5- to 7-membered ring which can contain at least one other heteroatom selected from oxygen, sulfur and nitrogen, said nitrogen optionally being substituted by a group R'", which is a linear or branched alkyl group containing from 1 to 6 carbon atoms, or
      a methacryloyl group or an acryloyl group,
      an aralkyl or heteroaralkyl group in which the alkyl group is linear or branched and contains from 1 to 4 carbon atoms and in which the aryl or heteroaryl moiety is as defined above for the aryl or heteroaryl group, or
    said two substituents R$_1$ and R$_2$ together form an adamantyl, norbornyl, fluorenylidene, di(C$_1$–C$_6$)alkylanthracenylidene or spiro(C$_5$–C$_6$)cycloalkylanthracenylidene group, said group optionally being substituted by at least one of the substituents listed above for R$_1$ and R$_2$ as an aryl or heteroaryl group;
  R$_3$, which are identical or different, independently are:
    a halogen, especially fluorine, chlorine or bromine,
    a hydroxy,
    a linear or branched alkyl group containing from 1 to 12 carbon atoms (advantageously from 1 to 6 carbon atoms),
    a cycloalkyl group containing from 3 to 12 carbon atoms,
    a linear or branched alkoxy group containing from 1 to 12 carbon atoms (advantageously from 1 to 6 carbon atoms),
    a haloalkyl, halocycloalkyl or haloalkoxy group corresponding respectively to the above alkyl, cycloalkyl and alkoxy groups substituted by at least one halogen atom selected especially from fluorine, chlorine and bromine,
    an aryl or heteroaryl group as defined above for R$_1$ and R$_2$,
    an aralkyl or heteroaralkyl group, the alkyl group, which is linear or branched, containing from 1 to 4 carbon atoms and the aryl and heteroaryl a groups being as defined above for R$_1$ and R$_2$,
    a phenoxy or naphthoxy group optionally substituted by at least one linear or branched alkyl or alkoxy group containing from 1 to 12 carbon atoms,
    one of the following amine or amide groups: —NH$_2$, —NHR, —CONH$_2$, —CONHR,

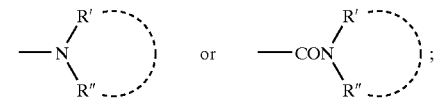

R, R' and R" respectively being as defined above for the amino substituents of R$_1$ and R$_2$ as aryl or heteroaryl, or a group —OCOR$_7$ or —COOR$_7$, R$_7$ being a linear or branched alkyl group containing from 1 to 6 carbon atoms, a cycloalkyl group containing from 3 to 6 carbon atoms or a phenyl group, optionally substituted by at least one of the substituents listed above for R$_1$ and R$_2$ as aryl or heteroaryl, or at least two adjacent groups R$_3$ together form an aromatic or non-aromatic cyclic group with one ring or two fused rings, which can contain at least one heteroatom selected from the group comprising oxygen, sulfur and nitrogen, it being possible for said ring(s), which are independently aromatic or non-aromatic and 5- to 7-membered, to contain at least one substituent selected from a group as defined above by way of substituents of the basic structure of the aryl or heteroaryl group representing R$_1$ or R$_2$; and m is an integer from 0 to 4.

Those skilled in the art will obviously have understood that the branched alkyl, alkoxy and alkenyl groups as defined above contain a sufficient number of carbons to be able to be branched (respectively more than 3, more than 3 and more than 4 carbon atoms).

The compounds of the invention—naphthopyrans of formula (I) or (II)—possess a high colorability associated with decolorization kinetics appropriate to the intended applications. The colors, which are readily accessible, vary from orange to violet.

Among said compounds of formula (I) or (II) of the invention, there are those in which:

X is an oxygen. Among these compounds, the following two subfamilies are very particularly preferred: the subfamily of compounds of formula (I) or (II) in which X=O, as stated, and R$_4$ and R$_5$ together form an oxo group, and the subfamily of compounds of formula (I) or (II) in which X=O, as stated, and R$_4$ and R$_5$ are hydrogens; and those in which:

X is a group NR$_6$. Among these compounds, the following three subfamilies are very particularly preferred: the subfamily of compounds of formula (I) or (II) in which X=NR$_6$, as stated, and R$_4$ and R$_5$ together form an oxo group, the subfamily of compounds of formula (I) or (II) in which X=NR$_6$, as stated, and R$_4$ and R$_5$ are hydrogens, and the subfamily of compounds of formula (I) or (II) in which X=NR$_6$, as stated, R$_4$ is a hydrogen and R$_5$ is a hydroxy.

With reference to the substituents R$_1$ and R$_2$, the preferred compounds of formula (I) or (II) are those in which:

R$_1$ and R$_2$ are identical or different and independently are optionally substituted aryl or heteroaryl groups whose basic structure is selected from the group comprising phenyl, naphthyl, biphenyl, pyridyl, furyl, benzofuryl, dibenzofuryl, N-(C$_1$–C$_6$)alkylcarbazole, thienyl, benzothienyl, dibenzothienyl and julolidinyl groups, R$_1$ and/or R$_2$ advantageously being a para-substituted phenyl group; or those in which:

R$_1$ and R$_2$ together form an adamantyl or norbornyl group.

In a first embodiment of the invention, the compounds (I) or (II) are such that at least two of their adjacent substituents R$_3$ do not together form a ring.

In a second embodiment of the invention, the compounds (I) and (II) are such that they comprise at least two adjacent groups R$_3$ which together form an aromatic or non-aromatic cyclic group with one ring or two fused rings, which can contain at least one heteroatom selected from the group comprising oxygen, sulfur and nitrogen, it being possible for said ring(s), which independently are aromatic or non-aromatic and 5- to 7-membered, to contain at least one substituent selected from a group as defined above by way of substituents of the basic structure of the aryl or heteroaryl group representing R$_1$ or R$_2$.

The compounds of the invention can be synthesized according to the following general scheme:

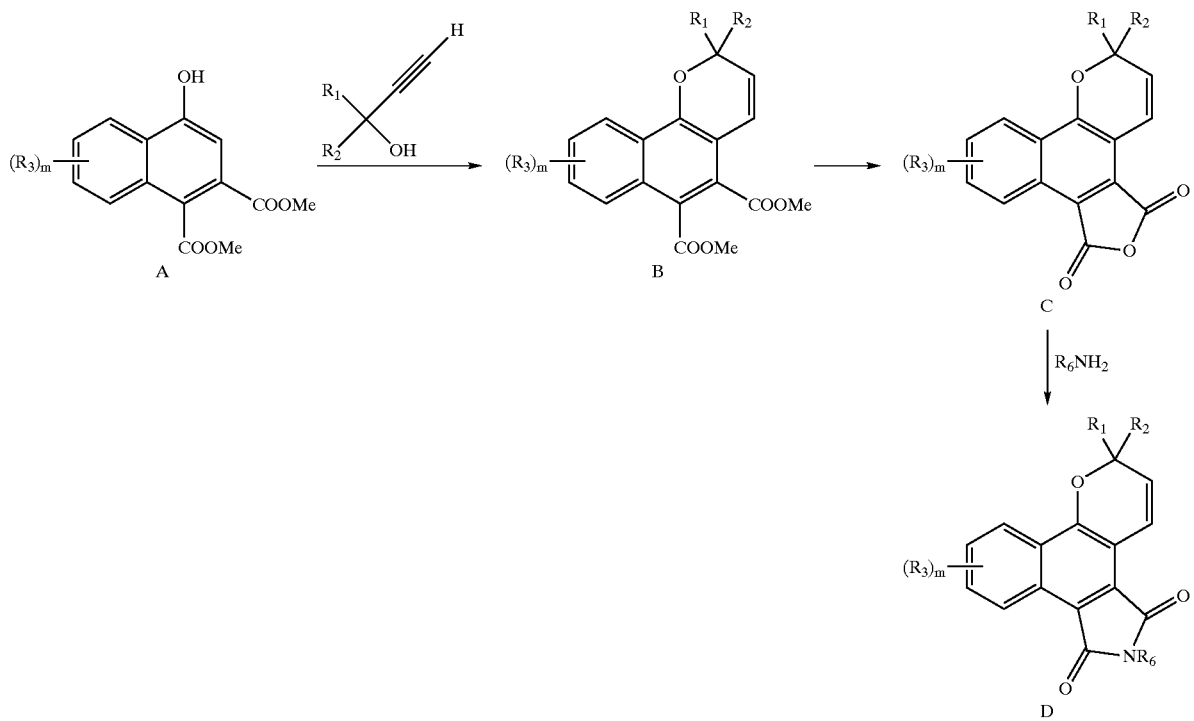

$R_1$, $R_2$, $R_3$, $R_6$ and m being as defined above with reference to formulae (I) and (II).

The starting materials A can be obtained by a procedure described by Kotsuki et al. (Bull. Chem. Soc. Jpn. 1994, 67, 599).

The intermediates B are obtained by processes well known to those skilled in the art (cf. e.g. EP-A-0 562 915 and U.S. Pat. No. 5,793,116).

The compounds C according to the invention are obtained by saponification of the esters in a basic medium, followed by a thermal cyclization-dehydration.

The compounds D according to the invention are obtained by condensing compounds C with a primary amine.

The other compounds of the invention in which $R_4$ and/or $R_5$=H or OH are obtained by reducing compounds C or D. Controlled reduction of the anhydrides (compounds C) with hydrides, such as $NaBH_4$ or $LiAlH_4$, yields lactones ($R_4$ and $R_5$=H) and/or hydroxyactones ($R_4$=H and $R_5$=OH) and controlled reduction of the imides yields lactams ($R_4$ and $R_5$=H) or hydroxyactams ($R_4$=H and $R_5$=OH) (cf. e.g. the following references: Bailey and Johnson, J. Org. Chem. 1970, 35, 3574 and Sato et al., Bull. Chem. Soc. Jpn. 1988, 61, 2238). Likewise, the anhydride or the imide is reacted with one or two equivalents of an organo-magnesium compound (alkylMgBr) to give the derivatives in which $R_4$=OH and $R_5$=alkyl or $R_4$=$R_5$=alkyl (cf. e.g. Zhang et al., J. Amer. Chem. Soc. 1993, 115, 3670–3673). The compounds in which $R_4$=H and $R_5$=alkyl (X=O or $NR_6$) can be synthesized according to the chemistry described by Canonne et al. in Tetrahedron 1988, 44, 2903.

According to a third feature, the invention relates to (co)polymers and/or crosslinked products obtained by the polymerization and/or crosslinking and/or grafting of at least one compound (I) or (II) as defined above. The compounds (I) or (II) according to the invention can be (co)monomers per se and/or can be included in (co)polymerizable and/or crosslinkable (co)monomers. The (co)polymers and/or crosslinked products obtained in this way can constitute photochromic matrices such as those presented below.

According to a fourth feature, the present invention relates to the use of said compounds of formula (I) or (II) of the invention as photochromic agents. The invention therefore further relates:

on the one hand to novel photochromic compounds which consist of the naphthopyran derivatives as defined above, taken in isolation or in a mixture with one another and/or with at least one other photochromic compound of a different type and/or with at least one non-photochromic coloring agent; and on the other hand to novel photochromic compositions which comprise at least one compound (I) or (II), as defined above, and/or at least one linear or crosslinked (co)polymer containing in its structure at least one compound (I) or (II) according to the invention. Such photochromic compositions can contain at least one other photochromic compound of a different type and/or at least one non-photochromic coloring agent and/or at least one stabilizer. These photochromic compounds of a different type, non-photochromic coloring agents and stabilizers are products of the prior art known to those skilled in the art.

Associations of photochromic compounds of the invention and/or associations of photochromic compounds of the invention and photochromic compounds of a different type, according to the prior art, are particularly recommended within the framework of the present invention, such associations being of value in that they are suitable for generating the gray or brown tints sought after by the public in applications such as ophthalmic lenses or sunglasses. These complementary photochromic compounds can be the ones known to those skilled in the art and described in the literature, for example chromenes (U.S. Pat. No. 3,567,605, U.S. Pat. No. 5,238,981, WO-A-94 22850, EP-A-0 562 915), spiropyrans or naphthospiropyrans (U.S. Pat. No. 5,238,981) and spiroxazines (CRANO et al., "*Applied Photochromic Polymer Systems*", published by Blackie & Son Ltd, 1992, chapter 2).

Said compositions according to the invention can also contain:

non-photochromic coloring agents for adjusting the tint, and/or one or more stabilizers, for example an antioxidant, and/or one or more UV inhibitors, and/or one or more free radical inhibitors, and/or one or more deactivators of photochemical excited states.

These additives can make it possible in particular to improve the durability of said compositions.

The compounds of the invention, envisaged within the framework of their photochromic applications, can be used in solution. Thus a photochromic solution can be obtained by solubilizing at least one of said compounds in an organic solvent such as toluene, dichloromethane, tetrahydrofuran or ethanol. The solutions obtained are generally colorless and transparent. They develop a strong coloration when exposed to sunlight and return to the colorless state when placed in a zone of lower exposure to solar radiation or, in other words, when they are no longer subjected to UV. A very low concentration of product (of the order of 0.01 to 5% by weight) is generally sufficient to obtain an intense coloration.

Furthermore, the compounds according to the invention are compatible with substrate matrices made of organic polymer or mineral (even hybrid) material, either included in said matrices or coated on said matrices.

Therefore, within the framework of the fourth feature of the invention pertaining to photochromic applications, the invention relates to a matrix containing:

at least one compound (I) or (II) as defined above, and/or at least one (co)polymer and/or crosslinked product as defined above, and/or at least one composition as presented above.

In fact, the most advantageous applications of the compounds of the invention are those in which the photochromic substance is uniformly dispersed within or over the surface of a matrix formed by a polymer and/or a copolymer and/or a mixture of (co)polymers.

Mirroring their behavior in solution, the compounds (I) or (II) included in a polymer matrix are colorless or slightly colored in the initial state and rapidly develop an intense coloration under UV light (365 nm) or a light source of the solar type. Finally, they return to their initial color when the irradiation ceases.

The processes which can be envisaged for obtaining such a matrix are very varied. An example which may be mentioned among the processes known to those skilled in the art is diffusion of the photochromic substance into the (co)polymer from a suspension or solution in a silicone oil, an aliphatic or aromatic hydrocarbon or a glycol, or from another polymer matrix. The diffusion is commonly carried out at a temperature of 50 to 200° C. for a period of 15 minutes to a few hours, depending on the nature of the polymer matrix. Another practical technique consists in mixing the photochromic substance into a formulation of polymerizable substances, depositing this mixture on a surface or in a mold and then performing the copolymerization. These and other practical techniques are described in the article by CRANO et al. entitled *"Spiroxazines and their use in photochromic lenses"* in Applied Photochromic Polymer Systems, published by Blackie & Son Ltd—1992.

The following products may be mentioned as examples of preferred polymer materials for forming matrices which can be used in optical applications of the photochromic compounds according to the invention:

alkyl, cycloalkyl, (poly or oligo)ethylene glycol, aryl or arylalkyl mono-, di-, tri- or tetraacrylate or mono-, di-, tri- or tetramethacrylate which is optionally halogenated or contains at least one ether and/or ester and/or carbonate and/or carbonate and/or thiocarbamate and/or urea and/or amide group, polystyrene, polyether, polyester, polycarbonate (e.g. polybisphenol-A carbonate, polydiallyldiethylene glycol carbonate), polycarbamate, polyepoxide, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutral, those obtained from difunctional monomers of the following formula:

$m_1$ and $n_1$ independently are integers between 0 and 4 inclusive and advantageously are independently equal to 1 or 2, X and X', which are identical or different, are a halogen, preferably a chlorine and/or a bromine, and $p_1$ and $q_1$ independently are integers between 0 and 4 inclusive, or copolymers of at least two types of copolymerizable monomers selected from the monomers which are precursors of the polymers listed above, preferably those belonging to the groups comprising (meth) acrylic, vinylic and allylic monomers and mixtures thereof.

Particularly preferably, the photochromic substances of the invention are used with resins which have a nanobiphase structure and are obtained by copolymerizing at least two specific, different difunctional monomers. Such resins have been described by the Applicant in patent application FR-A-2 762 845.

The amount of photochromic substance used in the (co)polymer matrix depends on the desired degree of darkening. The amount used is normally between 0.001 and 20% by weight.

Again according to the fourth feature pertaining to applications of the compounds (I) or (II) as photochromic substances, the present invention further relates to ophthalmic articles, such as ophthalmic lenses or sunglasses, comprising:

at least one compound (I) or (II) according to the invention, and/or at least one (co)polymer and/or crosslinked product at least partially formed by at least one compound of the invention, and/or at least one photochromic composition as defined above, and/or at least one matrix (as defined above) made of an organic polymer, a mineral material or a mineral-organic hybrid material, said matrix optionally comprising initially at least one compound of the invention.

In practice, the articles to which the present invention relates more particularly are photochromic ophthalmic lenses or sunglasses, glass panes (windows for buildings, locomotive engines, automotive vehicles), optical devices, decorative articles, articles for solar protection, data storage, etc.

The present invention is illustrated by the following Examples of the synthesis and photochromic validation of compounds of the invention. Said compounds of the invention are compared with compounds C1 and C2 of the prior art.

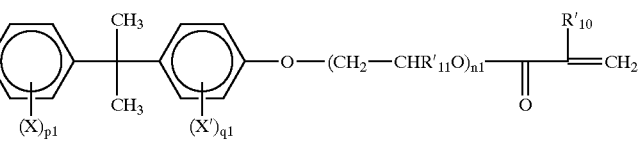

in which:

$R_{10}$, $R'_{10}$, $R_{11}$ and $R'_{11}$ are identical or different and independently are a hydrogen or a methyl group,

EXAMPLES

Example 1

Synthesis of the Compounds (1.D) and (1.E)

The compounds (1.D) and (1.E) were synthesized according to the following scheme:

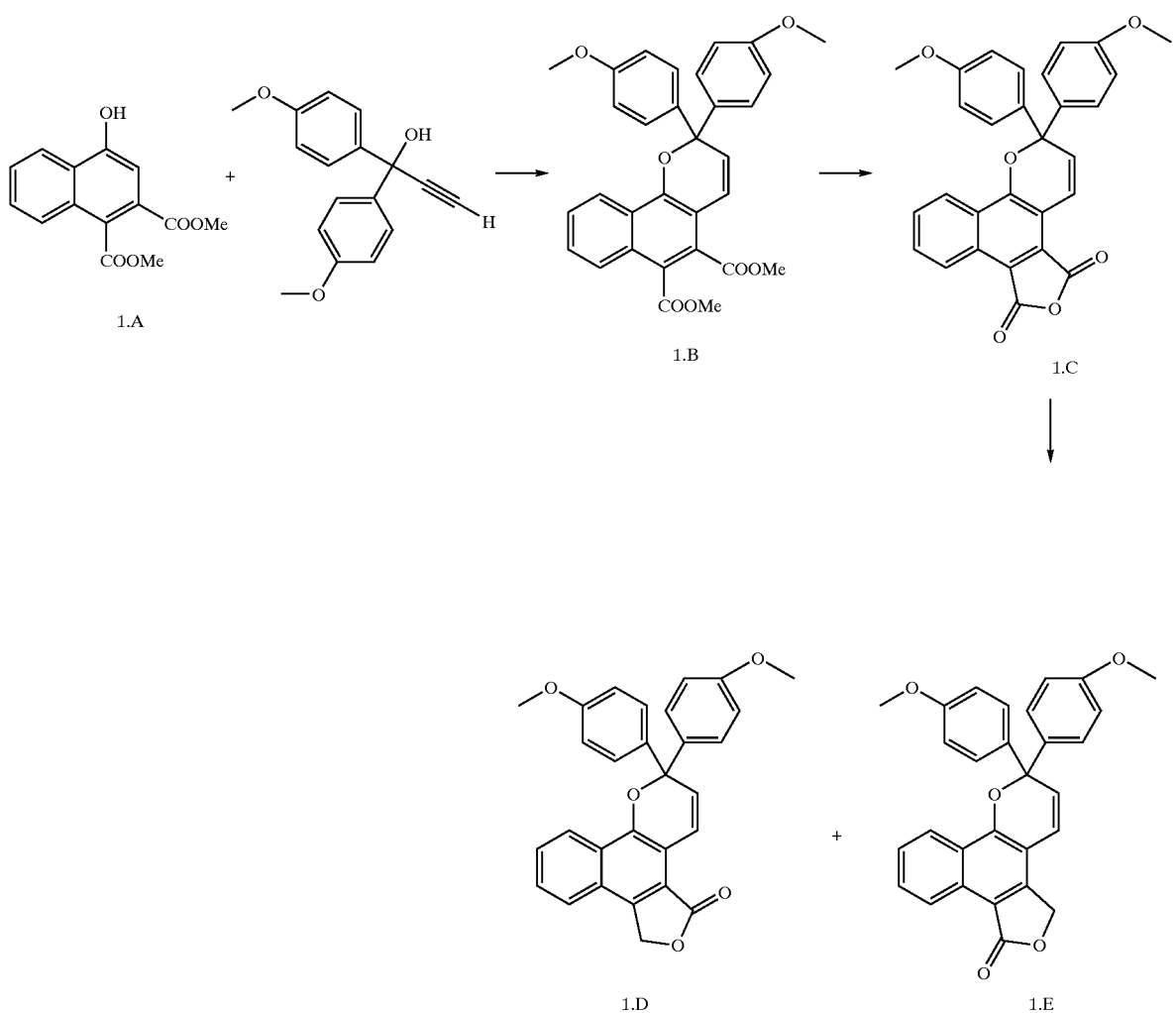

Step 1:

3.6 g of the naphthol 1.A (obtained by the process described by Kotsuki et al., Bull. Chem. Soc. Jpn. 1994, 67, 599) are reacted with 4.8 g of bis-1,1-(paramethoxyphenyl) propyn-1-ol in refluxing toluene for 4 hours in the presence of a catalytic amount of bromoacetic acid. After purification by chromatography on a silica column, 3 g of the intermediate 1.B are isolated.

Step 2:

The product 1.B is refluxed in ethanol in the presence of excess sodium hydroxide. The product is then isolated by acidification and extraction with toluene. The toluene solution is then refluxed for 6 hours with azeotropic distillation of water. After evaporation of the solvent and crystallization, 1.2 g of the compound (1.C) are isolated. Its structure is confirmed by proton NMR.

Step 3:

0.5 g of the compound (1.C) is solubilized in a THF/methanol mixture and then reduced by the addition of excess $NaBH_4$ at room temperature. The product is then purified by chromatography on silica. 230 mg of a mixture consisting of 30% of 1.D and 70% of 1.E are isolated. Their structures are confirmed by proton NMR.

Example 2

Synthesis of the Compounds (2.E) and (2.F)

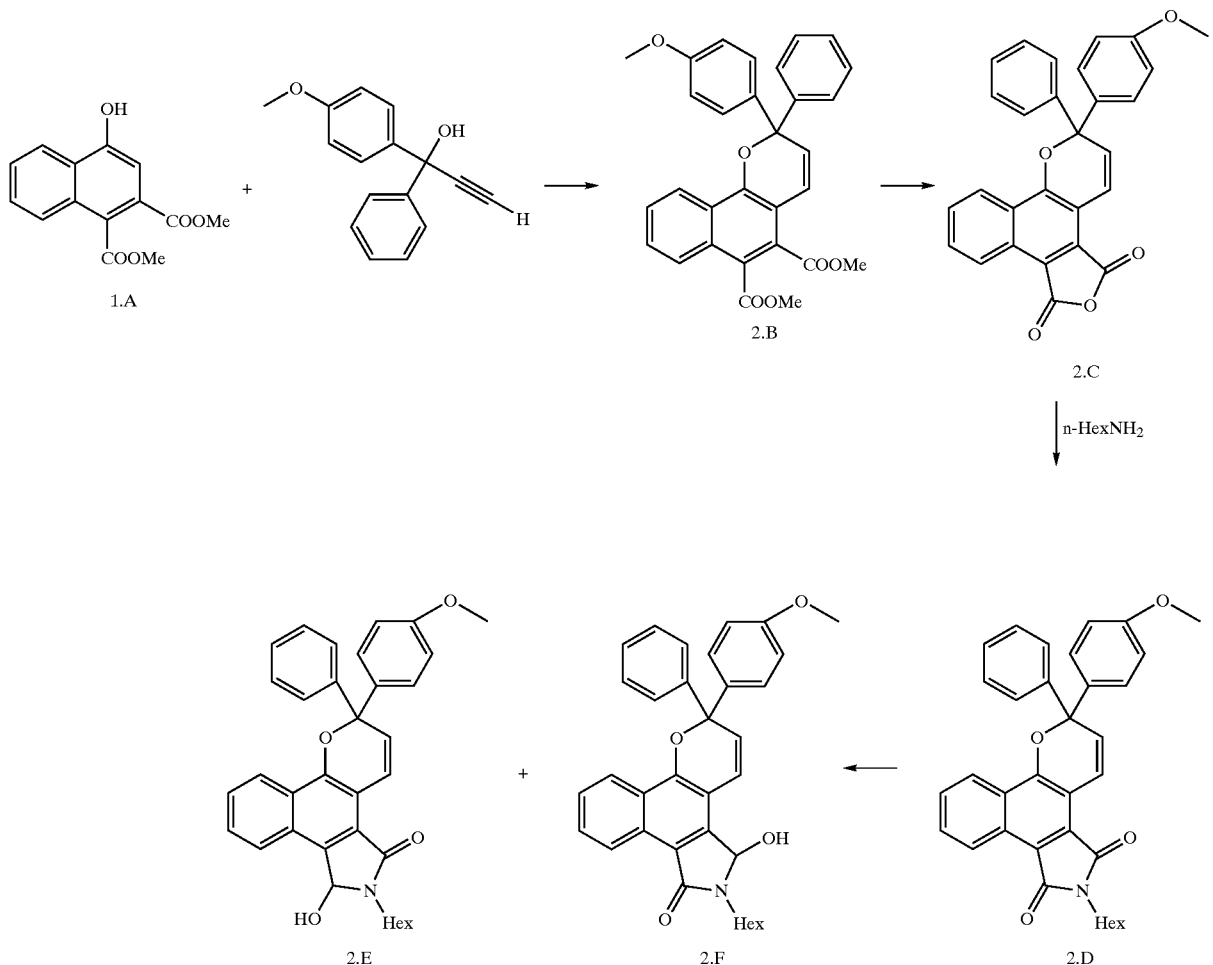

Step 1:

The derivative 2.C is synthesized as in Example 1 starting from 1-paramethoxyphenyl-1-phenylpropyn-1-ol.

Step 2:

0.65 g of the compound 2.C is reacted with 0.16 g of n-hexylamine in refluxing toluene for 2 hours. The reaction mixture is evaporated to dryness and the residue is refluxed again in 10 ml of xylene for 5 hours. After purification on a silica column, 0.75 g of the product 2.D is isolated.

Step 3:

0.75 g of the product 2.D is solubilized in a THF/methanol mixture (10+1 ml) and excess $NaBH_4$ is added in portions. After 20 minutes at room temperature, the product is purified by chromatography on silica. 50 mg of a mixture consisting of about 50% of 2.E and 50% of 2.F are isolated. Their structures are confirmed by proton NMR and mass spectrometry.

Example 3

Compounds C1 and C2

The compound C1 is commercially available. The compound C2 is described in patent U.S. Pat. No. 5,783,116.

Example 4

The photochromic properties of said compounds (1) [(1)=(1.D)+(1.E)], (2) [(2)=(2.E)+(2.F)], C1 and C2 were evaluated.

Said compounds are solubilized at a rate of 5 mg in 50 ml of THF and then the UV-visible absorptions are measured (optical path of 1 cm) before and after exposure to a 365 nm UV source. The tints and intensities developed are observed by placing the solutions in the sun or in a solar simulator. The properties of these compounds are given in the Table below.

| COMPOUND | STRUCTURE | λ 1* | T₁/₂** |
|---|---|---|---|
| 1.D + 1.E (30/70%) | | 500 nm | 9 s |
| 2E + 2F (50/50%) | | 512 nm | 20 s |
| C1 | 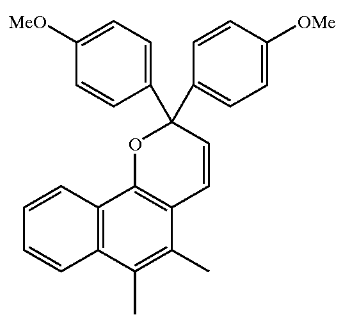 | 490 nm | 39 s |
| C2 | 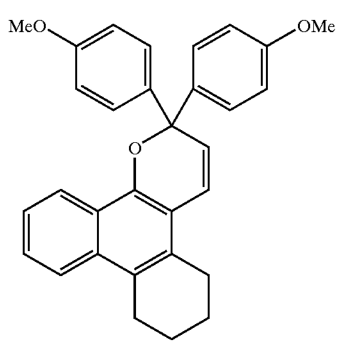 | 490 nm | 89 s |

*λ1 = maximum of the longest wavelength band of the compound after exposure.

**T$_{1/2}$ = decolorization time corresponding to a 50% drop in absorption at λ1$_{max}$.

Observation of the solutions in the presence of solar or UV radiation shows that the compounds of the invention have λ1 values shifted towards longer wavelengths (bathochromic shift) and have more rapid decolorization kinetics. This observation is particularly obvious when comparing the $\lambda_{max}$ values of the compounds (1) with those of the analogous compounds C1 and C2.

What is claimed is:

1. A compound having the formula (I) or (II) below:

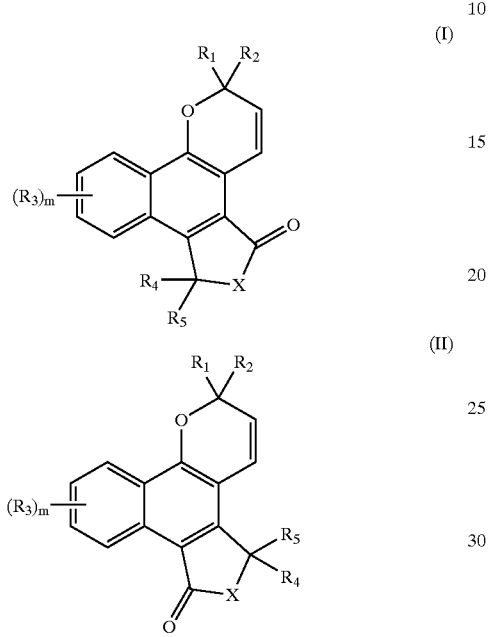

in which:
- X is an oxygen or $NR_6$, $R_6$ being a hydrogen, a linear or branched alkyl group comprising from 1 to 12 carbon atoms, a cycloalkyl group comprising from 3 to 12 carbon atoms, an aryl group comprising in its basic structure 6 to 24 carbon atoms, or a heteroaryl group comprising in its basic structure 4 to 24 carbon atoms and at least one heteroatom selected from the group consisting of sulfur, oxygen, and nitrogen, said aryl or heteroaryl group's basic structure optionally being substituted by at least one substituent selected from the group consisting of a linear or branched alkyl comprising 1 to 12 carbon atoms, a linear or branched alkoxy comprising 1 to 12 carbon atoms, a halogen, and a hydroxy;
- $R_4$ and $R_5$, which are identical or different, independently represent a hydrogen, a hydroxy, or a linear or branched alkyl group comprising 1 to 6 carbon atoms, or $R_4$ and $R_5$ together form an oxo group (=O);
- $R_1$ and $R_2$, which are identical or different, independently are:
  - hydrogen,
  - a linear or branched alkyl group comprising from 1 to 12 carbon atoms,
  - a cycloalkyl group comprising from 3 to 12 carbon atoms,
  - an aryl group comprising in its basic structure 6 to 24 carbon atoms or a heteroaryl group comprising in its basic structure 4 to 24 carbon atoms and at least one heteroatom selected from the group consisting of sulfur, oxygen, and nitrogen, said aryl or heteroaryl group's basic structure optionally being substituted with at least one substituent selected from the group consisting of:
    - a halogen,
    - a hydroxy,
    - a linear or branched alkyl group comprising from 1 to 12 carbon atoms,
    - a linear or branched alkoxy group comprising from 1 to 12 carbon atoms,
    - a haloalkyl or haloalkoxy group corresponding respectively to the above $(C_1-C_{12})$alkyl or $(C_1-C_{12})$alkoxy groups substituted with at least one halogen atom,
    - a phenoxy or naphthoxy group optionally substituted with at least one linear or branched alkyl or alkoxy group comprising from 1 to 12 carbon atoms,
    - a linear or branched alkenyl group comprising from 2 to 12 carbon atoms,
    - an —$NH_2$ group,
    - an —NHR group, wherein R is a linear or branched alkyl group comprising from 1 to 6 carbon atoms or a phenyl group optionally substituted by at least one linear or branched alkyl comprising from 1 to 6 carbon atoms,
    - a group having the formula:

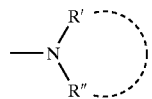

wherein R' and R", identical or different, independently represent a linear or branched alkyl group comprising from 1 to 6 carbon atoms or a phenyl group optionally substituted with at least one linear or branched alkyl comprising 1 to 6 carbon atoms, or R' and R", together with the nitrogen atom to which they are bonded, represent a 5- to 7-membered ring which optionally comprises at least one other heteroatom selected from the group consisting of oxygen, sulfur, and nitrogen, said nitrogen optionally being substituted with a group R''', which is a linear or branched alkyl group comprising from 1 to 6 carbon atoms, and
    - a methacryloyl group or an acryloyl group, or
  - an aralkyl or heteroaralkyl group in which the alkyl part is linear or branched and comprises from 1 to 4 carbon atoms and in which the aryl or heteroaryl part is as defined above for the aryl or heteroaryl group, or
- said two substituents $R_1$ and $R_2$ together form an adamantyl, norbornyl, fluorenylidene, di($C_1-C_6$)alkylanthracenylidene, or spiro($C_5-C_6$)cycloalkylanthracenylidene group, said group being optionally substituted with at least one of the substituents listed above for $R_1$ and $R_2$ as an aryl or heteroaryl group;
- $R_3$, which are identical or different, independently are:
  - a halogen,
  - a hydroxy,
  - a linear or branched alkyl group comprising from 1 to 12 carbon atoms,
  - a cycloalkyl group comprising from 3 to 12 carbon atoms,
  - a linear or branched alkoxy group comprising from 1 to 12 carbon atoms,
  - a haloalkyl, halocycloalkyl, or haloalkoxy group corresponding respectively to the above alkyl, cycloalkyl, and alkoxy groups substituted with at least one halogen atom, an aryl or heteroaryl group as defined above for $R_1$ and $R_2$, an aralkyl or heteroaralkyl group in which the alkyl part is linear or branched and comprises from 1 to 4 carbon atoms and in which the aryl or heteroaryl part is as defined above for $R_1$ and $R_2$, a phenoxy or naphthoxy group optionally substituted with at least one linear or branched alkyl or alkoxy group comprising from 1 to 12 carbon atoms, one of the following amine or amide groups: —$NH_2$, —NHR, —$CONH_2$, —CONHR,

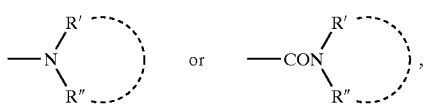

R, R', and R" respectively being as defined above for the amino substituents of $R_1$ and $R_2$ as aryl or heteroaryl, or a group —$OCOR_7$ or —$COOR_7$, wherein $R_7$ is a linear or branched alkyl group comprising from 1 to 6 carbon atoms, a cycloalkyl group comprising from 3 to 6 carbon atoms, or a phenyl group optionally substituted with at least one of the substituents listed above for $R_1$ and $R_2$ as aryl or heteroaryl, or at least two adjacent groups $R_3$ together form an aromatic or non-aromatic cyclic group having one ring or two fused rings which ring(s) are 5- to 7-membered, which ring(s) optionally comprise at least one heteroatom selected from the group consisting of oxygen, sulfur, and nitrogen, and which ring(s) are optionally substituted with at least one substituent selected from those given above in the definition for the aryl or heteroaryl groups which can form $R_1$ or $R_2$; and m is an integer from 0 to 4.

2. A compound according to claim 1 having formula (I).
3. A compound according to claim 1 having formula (II).
4. A compound according to claim 1, wherein X is an oxygen.
5. A compound according to claim 1, wherein X is an oxygen and $R_4$ and $R_5$ together form an oxo group.
6. A compound according to claim 1, wherein X is an oxygen and each of $R_4$ and $R_5$ is a hydrogen.
7. A compound according to claim 1, wherein X is an $NR_6$ group.
8. A compound according to claim 1, wherein X is an $NR_6$ group and $R_4$ and $R_5$ together form an oxo group.
9. A compound according to claim 1, wherein X is an $NR_6$ group and each of $R_4$ and $R_5$ is a hydrogen.
10. A compound according to claim 1, wherein X is an $NR_6$ group, $R_4$ is a hydrogen, and $R_5$ is a hydroxy.
11. A compound according to claim 1, wherein at least one of $R_1$ and $R_2$ is a para-substituted phenyl group.
12. A compound according to claim 1, wherein $R_1$ and $R_2$ are identical or different and independently represent optionally substituted aryl or heteroaryl groups whose basic structure is selected from the group consisting of those of phenyl, naphthyl, biphenyl, pyridyl, furyl, benzofuryl, dibenzofuryl, N-($C_1$–$C_6$)-alkylcarbazole, thienyl, benzothienyl, dibenzothienyl, and julolidinyl groups; or $R_1$ and $R_2$ together form an adamantyl or norbornyl group.

13. A compound according to claim 12 having formula.
14. A compound according to claim 12 having formula.
15. A compound according to claim 12, wherein X is an oxygen.
16. A compound according to claim 12, wherein X is an $NR_6$ group.
17. A (co)polymer and/or crosslinked product obtained by polymerizing and/or crosslinking and/or grafting at least one monomer comprising at least one compound according to claim 1.
18. A (co)polymer matrix which comprises:

at least one (co)polymer and/or crosslinked product according to claim 17.

19. A (co)polymer matrix according to claim 18, wherein the (co)polymer is selected from the group consisting of:

an alkyl, cycloalkyl, (poly or oligo)ethylene glycol, aryl or arylalkyl mono-, di-, tri- or tetra-acrylate or mono-, di-, tri- or tetra-methacrylate which is optionally halogenated or which optionally comprises at least one ether and/or ester and/or carbonate and/or carbamate and/or thiocarbamate and/or urea and/or amide group, a polystyrene, polyether, polyester, polycarbonate, polycarbamate, polyepoxide, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral, a (co)polymer obtained from a difunctional monomer of the following formula:

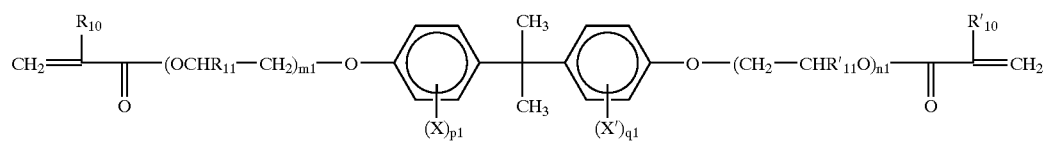

in which:

$R_{10}$, $R'_{10}$, $R_{11}$ and $R'_{11}$ are identical or different and independently are a hydrogen or a methyl group, $m_1$ and $n_1$ independently are integers between 0 and 4 inclusive, X and X', which are identical or different, are a halogen, and $p_1$ and $q_1$ independently are integers between 0 and 4 inclusive;

a copolymer of at least two types of copolymerizable monomers selected from the group consisting of the monomers which are precursors of the polymers listed above; and combinations thereof.

20. A photochromic compound which is constituted by a compound according to claim 1, or by a mixture of at least two compounds according to claim 1, or by a mixture of at least one compound according to claim 1 and at least one other photochromic compound of a different type and/or at least one non-photochromic coloring agent.

21. A photochromic composition which comprises:
at least one compound according to claim 1, and/or
at least one linear or crosslinked (co)polymer which contains, in its structure, at least one compound according to claim 1, and
optionally, at least one other photochromic compound of a different type and/or at least one non-photochromic coloring agent and/or at least one stabilizer.

22. A (co)polymer matrix which comprises:
at least one photochromic composition according to claim 21.

di-, tri- or tetra-methacrylate which is optionally halogenated or which optionally comprises at least one ether and/or ester and/or carbonate and/or carbamate and/or thiocarbamate and/or urea and/or amide group,
a polystyrene, polyether, polyester, polycarbonate, polycarbamate, polyepoxide, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral,
a (co)polymer obtained from a difunctional monomer of the following formula:

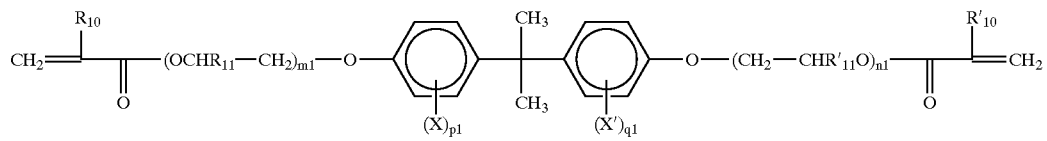

23. A (co)polymer matrix according to claim 22, wherein the (co)polymer is selected from the group consisting of:
an alkyl, cycloalkyl, (poly or oligo)ethylene glycol, aryl or arylalkyl mono-, di, tri-, or tetra-acrylate or mono, di-, tri or tetra-methacrylate which is optionally halogenated or which optionally comprises at least one ether and/or ester and/or carbonate and/or carbamate and/or thiocarbamate and/or urea and/or amide group,
a polystyrene, polyether, polyester, polycarbonate, polycarbamate, polyepoxide, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral,
a (co)polymer obtained from a difunctional monomer of the following formula:

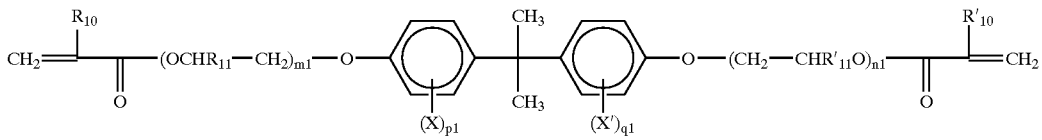

in which:
$R_{10}$, $R'_{10}$, $R_{11}$ and $R'_{11}$ are identical or different and independently are a hydrogen or a methyl group,
$m_1$ and $n_1$ independently are integers between 0 and 4 inclusive,
X and X', which are identical or different, are a halogen, and
$p_1$ and $q_1$ independently are integers between 0 and 4 inclusive;
a copolymer of at least two types of copolymerizable monomers selected from the group consisting of the monomers which are precursor of the polymers listed above; and
combinations thereof.

24. A (co)polymer matrix which comprises;
at least one compound according to claim 1.

25. A (co)polymer matrix according to claim 24, wherein the (co)polymer is selected from the group consisting of:
an alkyl, cycloalkyl, (poly or oligo)ethylene glycol, aryl or arylalkyl mono-, di-, tri-, or tetra-acrylate or mono-, in which:
$R_{10}$, $R'_{10}$, $R_{11}$ and $R'_{11}$ are identical or different and independently are a hydrogen or a methyl group,
$m_1$ and $n_1$ independently are integers between 0 and 4 inclusive,
X and X', which are identical or different, are a halogen, and
$p_1$ and $q_1$ independently are integers between 0 and 4 inclusive;
a copolymer of at least two types of copolymerizable monomers selected from the group consisting of the monomers which are precursors of the polymers listed above; and
combinations thereof.

26. An ophthalmic or solar article comprising:
at least one compound according to claim 1.

27. An article according to claim 26, wherein said article is selected from the group consisting of a lens, a glass pane, and an optical device.

28. An ophthalmic or solar article comprising:
at least one (co)polymer and/or crosslinked product according to claim 17.

29. An article according to claim 28, wherein said article is selected from the group consisting of a lens, a glass pane, and an optical device.

30. An ophthalmic or solar article comprising:
at least one matrix according to claim 18.

31. An article according to claim 30, wherein said article is selected from the group consisting of a lens, a glass pane, and an optical device.

32. An ophthalmic or solar article comprising:
at least one at least one photochromic composition according to claim 21.

33. An article according to claim 32, wherein said article is selected from the group consisting of a lens, a glass pane, and an optical device.

34. An ophthalmic or solar article comprising:

at least one matrix according to claim 22.

35. An article according to claim 34, wherein said article is selected from the group consisting of a lens, a glass pane, and an optical device.

36. An ophthalmic or solar article comprising:

at least one matrix according to claim 24.

37. An article according to claim 36, wherein said article is selected from the group consisting of a lens, a glass pane, and an optical device.

* * * * *